United States Patent [19]

Wessendorf et al.

[11] 4,065,506
[45] Dec. 27, 1977

[54] CONTINUOUS PROCESS FOR REFINING GLYOXAL

[75] Inventors: Richard Wessendorf, Essen-Heisingen; August Sommer, Herne; Heinrich Birkelbach, Oer-Erkenschwick, all of Germany

[73] Assignee: Veba-Chemie AG, Gelsenkirchen-Buer, Germany

[21] Appl. No.: 573,197

[22] Filed: Apr. 30, 1975

[30] Foreign Application Priority Data

June 11, 1974 Germany .............................. 2428081

[51] Int. Cl.² .............................................. C07C 47/02
[52] U.S. Cl. ................................................ 260/601 R
[58] Field of Search .......................... 260/60 R, 601 R

[56] References Cited

U.S. PATENT DOCUMENTS

| 2,339,346 | 1/1944 | McNamee et al. | 260/603 HF |
|---|---|---|---|
| 3,367,973 | 2/1968 | Schramm et al. | 260/602 |
| 3,542,879 | 12/1970 | Dinwoodie et al. | 260/601 R |
| 3,574,765 | 4/1971 | Kuryla et al. | 260/601 R |

*Primary Examiner*—James O. Thomas, Jr.
*Assistant Examiner*—W. B. Lone
*Attorney, Agent, or Firm*—Burgess, Dinklage & Sprung

[57] ABSTRACT

An improvement in a process for refining crude glyoxal solutions, especially those obtained by the oxidation of acid aldehyde with nitric acid, wherein the crude glyoxal solution, free of volatile acids, is neutralized, the glyoxal is transformed to the glyoxal semiacetal with an alcohol having 1 to 3 carbon atoms and, after separation of the salts and other impurities, is again hydrolized with water at elevated temperatures. The improvement described involves continuously extracting the glyoxal semiacetal formed with an organic solvent which is immiscible with water, hydrolyzing the extracted glyoxal semiacetal and refining the aqueous glyoxal solution obtained with active charcoal.

7 Claims, No Drawings

CONTINUOUS PROCESS FOR REFINING GLYOXAL

BACKGROUND

Copending application Ser. No. 478,431, filed June 11, 1974, now U.S. Pat. No. 4,006,189 relates to a process for the purification of glyoxal solutions, especially those which have been obtained by the oxidation of acetaldehyde with nitric acid, the raw glyoxal solution, freed of the volatile acids, being neutralized, the glyoxal being transformed to the glyoxal semiacetal with an alcohol having 1 to 3 carbon atoms, with removal of the water, and, after separation of the salts and other impurities, being hydrolyzed again with water at elevated temperature.

The present invention relates to an improved process for the purification of glyoxal and consists in a continuous process whereby technical raw glyoxal solutions are made into acid-free and colorless aqueous glyoxal solutions.

Glyoxal is prepared technically by the oxidation of acetaldehyde with aqueous nitric acid. The raw product thus produced contains, in addition to the unreacted starting substances acetaldehyde and nitric acid, a number of by-products whose complete separation presents considerable difficulty.

The acids involved are acids which are volatile at elevated temperatures, namely acetic acid and formic acid, acids of low volatility, namely glyoxalic acid, glycolic acid and oxalic acid, and also inorganic electrolytes and other impurities which cause a more or less great discoloration of the product.

It is possible to remove most of the volatile acids by distillation and concentration of the solution, but a crude glyoxal is obtained from which the remaining acid cannot be removed by this method.

In older processes, these acids are neutralized with carbonates of a metal of the Second Group, especially calcium carbonate; however, the separation of the calcium salts in solid form is incomplete, so that the solution is additionally contaminated with calcium ions. The glyoxal solutions thus refined have a strong yellow discoloration.

Attempts have also been made to remove the nonvolatile acids with ion exchangers, for example in accordance with German Auslegeschrift No. 1,154,081.

If one compares the acid content of a crude glyoxal solution subjected to preliminary purification by distillation with the capacities of an anion exchanger ($\sim$1.5 val/l) it will be seen that, for the deacidification of a 40% crude glyoxal solution (D 1.27), an equal volume of the ion exchange resin will be required. Then, the fact that the removal of the glyoxal solution from an exhausted anion exchange resin requires a six-fold to ten-fold volume of washing liquid, and an equal volume of washing liquid will again be consumed after the resin is regenerated with caustic soda solution, places a considerable burden on the economy of this method.

The high water consumption will be disadvantageous even in the electrolytic dialysis method described in German Auslegeschrift No. 1,618,281. The authors achieve a glyoxal yield of 80 to 90% at a detention time of 20 hours.

In the method of Russian Pat. No. 168,670, the crude glyoxal and ethanol are used to prepare first the tetraacetal which, after being refined by distillation, is hydrolyzed on acid cation exchangers. However, according to our own experiments and reports given in the literature (J. Am. Chem. Soc. 77, 1285, 1955), the acetal formation is unsatisfactory even with a great excess of alcohol.

German Offenlegungsschrift No. 2,159,975 describes the preparation and use of glyoxal semiacetals and also the use of glyoxal semiacetals as intermediates for the production of acid-free, aqueous glyoxal solutions. In this procedure the starting products are technical glyoxal solutions from which the glyoxal semiacetals are isolated by reaction with alcohols which are not miscible in water, and are purified. In a three-stage hydrolysis with boiling water, however, only 80% can be obtained as hydrate. The solution obtained still contains definite traces of the alcohol put in. The essential disadvantages of the described method is the incomplete separation of the glyoxal from its solution, which has not been achieved even when an excess of the alcohol was used.

In the method of copending application Ser. no. 478,431, now U.S. Pat. No. 4,006,189 technical crude glyoxal solutions, after separation of the volatile acids, are neutralized, the glyoxal is transformed to the glyoxal semiacetal with an alcohol having 1 to 3 carbon atoms with removal of the water, and after separation of the salts and other impurities it is rehydrolyzed with water at elevated temperature.

THE INVENTION

It has now been found that a continuous purification of the crude glyoxal can be accomplished advantageously by extracting the glyoxal as glyoxal semiacetal from the aqueous, neutralized solution with the aid of an appropriate solvent, and then transforming it back to the glyoxal hydrate by hydrolysis.

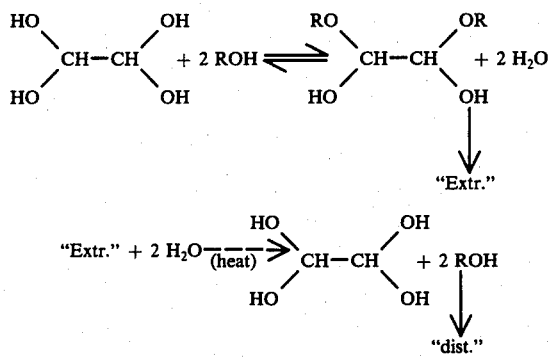

The subject matter of the invention is therefore a method of refining crude glyoxal solutions, especially those which have been obtained by the oxidation of acetaldehyde with nitric acid, the crude glyoxal solution, freed of the volatile acids, being neutralized, the glyoxal being transformed to the glyoxal semiacetal with an alcohol having 1 to 3 carbon atoms, and, after separation of the salts and other impurities, being hydrolyzed again with water at elevated temperature, in accordance with copending application Ser. No. 478,431, characterized in that the glyoxal semiacetal that is formed is continously extracted with an organic solvent which is not miscible with water, the extracted glyoxal semiacetal is subjected to hydrolysis, and the aqueous glyoxal solution thus obtained is purified with active charcoal.

DESCRIPTION

The solvent that is used for the extraction can be removed either by distillation or by re-extraction.

Although a complete dehydration would shift the equilibrium towards the formation of the semiacetal, the extraction of the semiacetals is performed at a water content at which a liquid-to-liquid extraction is still practicable. In this manner a convenient separation of the undesired by-products in dissolved form is possible. The refining process of the invention is performed in the following steps:

1. Neutralization of the concentrated crude glyoxal solution
2. Formation of glyoxal semiacetal and extraction
3. Hydrolysis of the glyoxal semiacetal solution with recovery of the solvent and of the alcohol.

In the first step, the solution to be refined is reacted with a concentrated lye, such as potash lye or soda lye, or with a suspension of calcium hydroxide, so that a pH of 6 to 6.5 is measured. At the same time the solution is vigorously stirred and maintained at a temperature below 20° C in order to suppress the Cannizzaro reaction, the formation of salts of glycolic acid from the glyoxal. The neutralization can be performed in conventional reactors equipped with a cooling apparatus, but it is advantageous to use "in-line mixers," which perform this step of the process continuously, in a simple manner. The formation of glyoxal semiacetal and extraction from the aqueous solution, which follows, is performed in the second step of the process, in which the glyoxal solution is treated with an appropriate extractant which contains the alcohol needed for the semiacetal formation.

The extractant can be a solvent which is insoluble or only sparingly soluble in water, has a good ability to dissolve glyoxal semiacetals, and is easy to separate from the aqueous glyoxal solution in the hydrolysis. It must furthermore not be a solvent for the by-products which are to be separated when it is mixed with the alcohols used for the formation of the semiacetal. A benzene-benzine mixture is especially suitable, but so are halogenated hydrocarbons such as methylene chloride, ethylene chloride and carbon tetrachloride and aromatic hydrocarbons such as toluene and ethylbenzene and cycloaliphatic hydrocarbons such as cyclohexane.

For the formation of the glyoxal semiacetal, alcohols of 1 to 3 carbons atoms are used principally, but higher alcohols can also be used; isopropyl alcohol is especially suitable.

The extraction can be performed either by a continuous step-wise method, that is, by periodical decanting from a series of separating vessels known as mixer-settler apparatus, or by continuous counterflow extraction in apparatus which have been developed in the art for this purpose. One important requirement for continuous extraction is a difference in the density of the phases which are in the exchange, so that a rapid and clean separation can be performed after vigorous mixing. Apparatus suitable for the liquid-to-liquid extraction are described in C.Z.-Chemie-Technik 1 (1972) 8, pp. 353 to 357, and elsewhere.

The hydrolysis of the extraction solution is performed in the third step of the process. It is accomplished by treating the extraction solution with water at elevated temperature and removing the solvent and alcohol by distillation. The aqueous glyoxal solution will remain in the body of the still.

This step, too, can be performed continuously be feeding the extraction solution together with the required amount of water into a distillation column, from the top of which the solvent-alcohol-water mixture is withdrawn, and the aqueous glyoxal solution is obtained as the sump product.

During the distillative separation of the solvent and of the alcohol during the hydrolysis procedure it is inevitable that considerable amounts of water will accompany them as a component of an azeotrope. It is therefore advantageous to recover the solvent in a continuous re-extraction with water.

In the hydrolysis, then, the alcohol is separated by distillation, and it is dehydrated in a subsequent column and can be reused. The aqueous glyoxal solution obtained from the hydrolysis reaction is advantageously filtered through active charcoal before the adjustment of the desired glyoxal concentration.

EXAMPLES

The process will be further explained with the aid of the following examples.

EXAMPLE 1

Continuous step-wise refinement of crude glyoxal.

A concentrated crude glyoxal solution (acid number 114) was adjusted with 30% caustic soda solution, with stirring and cooling, to a pH of 6.2, the temperature of the solution not rising above 18° C.

To 55.1 g of this neutralized crude glyoxal solution (53.2% glyoxal) in an 300-ml Erlenmeyer flask equipped with a reflux condenser there was added 185 g of extractant having the following composition:

32.5% isopropyl alcohol
21.6% benzene
43.2% benzine
2.7% water

The mixture was vigorously stirred for 30 minutes at 50° C by means of a magnetic stirrer.

After the mixture had cooled, the upper phase could be separated by careful decantation. The remaining lower phase was treated three more times in the same manner. The result of this extraction is summarized in the following table:

|  | Lower Phase | | Upper Phase | |
|---|---|---|---|---|
|  | Starting Quantity g | Glyoxal g | Starting Quantity g | Glyoxal g |
| Before extraction | 55.1 | 29.3 | 185 | — |
| After 1st extraction | 34.3 |  | 206.6 | 20.2 |
| After 2nd extraction | 26.6 |  | 192.7 | 5.85 |
| After 3rd extraction | 23.2 |  | 188.8 | 1.90 |
| After 4th extraction | 21.7 | 0.8 | 187.3 | 0.47 |
|  |  |  |  | 28.42 |

28.42 g of glyoxal was obtained from the crude glyoxal solution, which corresponds to a yield of 97% of the theory.

EXAMPLE 2

Continuous refinement of crude glyoxal using an extraction column.

2.1 Preparation of the glyoxal semiacetal solution

A jacketed extraction column for the counterflow liquid-to-liquid extraction (length 3 m, inside diameter 40 mm, filled with Braunschweig coils 4 × 4), was filled with the extractant (cf. Example 1) and heated to 50° C by means of a circulating liquid heating system.

333 ml (490 g) of crude glyoxal solution was fed to the top of the column hourly by means of a proportioning pump, the solution being finely divided by a frit in the light phase. At the same time, 2000 ml (1520 g) of extractant was fed hourly into the sump of the extraction column above the settling zone. In addition to the counterflow movement, the contents of the column were vibrated by a pulsator (amplitude about 6 mm, 75 pulsations per minute).

After 8 hours, the extraction column was in equilibrium, i.e., the glyoxal concentration of the extractant leaving at the top of the extraction column amounted unvaryingly to 12.4% and therefore contained 93% of the glyoxal put into the refining process.

The extracted aqueous phase could be withdrawn continuously from the sump of the extraction column.

2.2 -Hydrolysis of the Glyoxal Semiacetal Solution

In a distillation apparatus consisting of a 2-liter sump body, a 2-meter bell-shaped tray column with a silver mirrored high-vacuum jacket, a column feed in the center of the column, and a cacuum column head, 1000 ml of water was placed and heated at a pressure of 160 Torr by means of an oil bath, with refluxing. Then a glyoxal semiacetal solution (glyoxal content 12.4%) preheated to 50° C was added drop by drop in the center of the column such that a fraction having a boiling point from 54° to 55° C was drawn off at the top (without refluxing).

The distillate could be reused, after dehydration, for the extraction. As soon as a glyoxal concentration of 30% had been reached in the sump, a corresponding amount of water was fed into the center of the column as required for the maintenance of this glyoxal concentration.

EXAMPLE 3

3.1 Recovery of the Solvent by Re-extraction

A glyoxal solution prepared as in Example 2.1 had the following composition :
13.8% glyoxal
28.1% isopropyl alcohol
18.8% benzene
37.6% benzine
1.7% water 330 g of water was fed hourly into the extraction column (cf. Example 2.1, but 20° C) at the top, and 1030 g of the glyoxal solution was fed hourly into the sump, the benzine-benzene mixture being simultaneously drawn from the upper settling tank, and a glyoxal solution being withdrawn from the lower settling zone.

After 1 to 3 hours of throughput, the composition of the upper phase was virtually constant and had the following analysis:
67.7% benzine
32.2% benzene
0.06% isopropyl alcohol
0.03% glyoxal
0.006% water The liquid withdrawn from the sump was not of constant composition until after about 10 hours of operation, and then it has the following composition:
36.5% isopropyl alcohol
18.02% glyoxal
1.14% benzene
Balance: water.

After another 5 hours the benzene content had dropped to 0.6 to 0.8%.

The upper phase could be re-used directly for the extraction.

3.2 Continuous Hydrolysis

The liquid withdrawn from the sump of the re-extraction column was preheated to 90° to 03° C and continuously fed into the upper third of a column (length 3.5 m, packed with 8 × 8 coils) which was heated in the sump for the production of steam from a 4-liter flask charged with 2.5 liters of water, at a bath temperature of 145° C.

The head product was an azeotropic mixture of the following composition:
82.9% isopropyl alcohol
3.8% benzene
0.3% benzine
12.6% water.

From a side tap at the foot of the column the dilute glyoxal solution was continuously removed. After brief treatment with active charcoal (0.5% with respect to the solution), followed by filtration, the solution was adjusted by distillation to a glyoxal content of 40% by weight. The color number was measured at 10 APHA.

What is claimed is:

1. A process for refining a crude glyoxal solution, especially one obtained by oxidation of acetaldehyde with nitric acid, containing volatile and non-volatile acids which consists essentially of:
   A. Distillatively freeing the crude glyoxal solution of volatile acids, and neutralizing the resultant solution by addition of a basic agent at a temperature below 20° C;
   B. Contacting the glyoxal with an alcohol having 1 to 3 carbon atoms whereby to form a glyoxal semiacetal of the formula

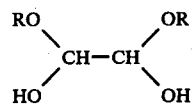

wherein R is $C_1$-$C_3$ alkyl;
   C. Continuously extracting said glyoxal semiacetal with an organic solvent selected from the group consisting of benzene-benzine mixture, methylene chloride, ethylene chloride, carbon tetrachloride, toluene, ethylbenzene and cyclohexane which is immiscible with water;
   D. Thereafter hydrolyzing the extracted glyoxal semiacetal by contacting the same with water.

2. Process of claim 1 wherein the solvent used for the extraction is removed by distillation, the neutralization is effected at room temperature and the extraction is effected at 50° C.

3. Process of claim 1 wherein the solvent used for the extraction is separated by re-extraction with water.

4. Process of claim 1 wherein the organic solvent is a mixture of benzene and benzine.

5. A process according to claim 1 wherein thereafter the hydralyzed material from step D is passed over active charcoal.

6. A process according to claim 1 wherein steps B and C are performed simultaneously.

7. A process according to claim 1 wherein the alcohol employed in step B is isopropyl alcohol.

* * * * *

UNITED STATES PATENT AND TRADEMARK OFFICE
CERTIFICATE OF CORRECTION

PATENT NO. : 4,065,506
DATED : December 27, 1977
INVENTOR(S) : Richard Wessendorf et al It is certified that error appears in the above-identified patent and that said Letters Patent are hereby corrected as shown below:

Column 2, line 16, "disadvantages" should read -- disadvantage --.

Column 4, line 3, "be" should read -- by --.

Column 5, line 25, "cacuum" should read -- vacuum --.

Column 6, line 62, "hydralyzed" should read -- hydrolyzed --.

Signed and Sealed this

First Day of August 1978

[SEAL]

Attest:

RUTH C. MASON
Attesting Officer

DONALD W. BANNER
Commissioner of Patents and Trademarks